United States Patent
Schmidlin et al.

(10) Patent No.: US 9,739,762 B2
(45) Date of Patent: Aug. 22, 2017

(54) PORTABLE SENSOR DEVICE WITH A GAS SENSOR AND LOW-POWER MODE

(71) Applicant: Sensirion AG, Stafa (CH)

(72) Inventors: Roger Schmidlin, Zurich (CH); Markus Graf, Zurich (CH)

(73) Assignee: Sensirion AG, Stafa (CH)

( * ) Notice: Subject to any disclaimer, the term of this patent is extended or adjusted under 35 U.S.C. 154(b) by 247 days.

(21) Appl. No.: 14/160,758

(22) Filed: Jan. 22, 2014

(65) Prior Publication Data
US 2014/0216129 A1    Aug. 7, 2014

(30) Foreign Application Priority Data
Jan. 31, 2013    (EP) ..................... 13405023

(51) Int. Cl.
*G01N 33/00*    (2006.01)

(52) U.S. Cl.
CPC ..... *G01N 33/0062* (2013.01); *G01N 33/0063* (2013.01); *H04M 2250/12* (2013.01)

(58) Field of Classification Search
CPC ............. G01N 21/3504; G01N 27/122; G01N 27/4163; G01N 33/0031; G01N 33/497
See application file for complete search history.

(56) References Cited

U.S. PATENT DOCUMENTS

| | | | |
|---|---|---|---|
| 6,382,198 B1* | 5/2002 | Smith ................. | F02D 41/0085 123/673 |
| 6,428,684 B1* | 8/2002 | Warburton ......... | G01N 27/4163 204/401 |
| 6,690,569 B1 | 2/2004 | Mayer et al. | |
| 6,792,794 B2* | 9/2004 | Bonne ................ | G01N 1/24 73/25.01 |
| 8,373,568 B2* | 2/2013 | Moe .................. | G08B 21/16 340/632 |
| 2003/0206325 A1* | 11/2003 | Sachse ............... | G01N 21/3504 359/246 |
| 2004/0016228 A1* | 1/2004 | Yasui ................. | G01N 27/4067 60/285 |
| 2004/0112117 A1* | 6/2004 | Wright .............. | G01N 33/0014 73/25.01 |
| 2004/0192412 A1 | 9/2004 | Ono et al. | |

(Continued)

FOREIGN PATENT DOCUMENTS

| | | | | |
|---|---|---|---|---|
| WO | | 9519563 | 7/1995 | |
| WO | | 2008020223 | 2/2008 | |
| WO | WO 2010150969 A1 * | | 12/2010 | ........... G01N 27/407 |

OTHER PUBLICATIONS

A. Mane, et al., "Explosive Detection With Mobile Telephony an Attempt Towards a Safe Ambience", International Conference on Signal Processing, Communication, Computing and Networking Technologies (ICSCCN), 2011, pp. 187-191.

*Primary Examiner* — David A Rogers
(74) *Attorney, Agent, or Firm* — Cooper & Dunham LLP

(57) ABSTRACT

A mobile device comprises a CPU operating a display and other user interface circuitry. Further, it comprises a gas sensor as well as a sensor hub connecting the gas sensor and other sensors to the CPU. In order to save power, the device can be brought into a low-power operating mode, where the CPU is idling or switched-off and the gas sensor itself has a low-power and a high-power operating mode. However, even in this low-power operating mode, the sensor hub still monitors for changes of the signal from the gas sensor and wakes the device up if such a change is detected.

12 Claims, 3 Drawing Sheets

(56) References Cited

U.S. PATENT DOCUMENTS

| | | | |
|---|---|---|---|
| 2005/0200475 A1* | 9/2005 | Chen | G08B 17/10 340/521 |
| 2006/0011476 A1* | 1/2006 | Hada | G01N 27/4065 204/406 |
| 2009/0044612 A1* | 2/2009 | Schoenthaler | F02D 41/146 73/114.71 |
| 2009/0152130 A1* | 6/2009 | Schneider | G01N 27/419 205/781 |
| 2010/0074157 A1* | 3/2010 | Doh | H04W 84/18 370/311 |
| 2010/0089122 A1* | 4/2010 | Abdullah | G01N 27/122 73/25.05 |
| 2011/0100090 A1* | 5/2011 | Zanella, Sr. | G01N 27/16 73/23.31 |
| 2011/0125414 A1* | 5/2011 | Schumann | G01N 27/4065 702/24 |
| 2011/0144515 A1 | 6/2011 | Bayer et al. | |
| 2011/0279129 A1* | 11/2011 | Suzuki | G01N 27/4065 324/649 |
| 2012/0270611 A1 | 10/2012 | Choi et al. | |
| 2013/0135782 A1* | 5/2013 | Roth | G01K 7/16 361/103 |
| 2013/0218524 A1* | 8/2013 | Faerevaag | G05B 19/0423 702/189 |
| 2014/0179298 A1* | 6/2014 | Grokop | G01S 19/48 455/418 |
| 2014/0257127 A1* | 9/2014 | Smith | A61B 5/082 600/532 |
| 2015/0120336 A1* | 4/2015 | Grokop | B60W 40/09 705/4 |

\* cited by examiner

PORTABLE SENSOR DEVICE WITH A GAS SENSOR AND LOW-POWER MODE

TECHNICAL FIELD

The invention relates to a portable electronic device, in particular to a mobile phone or a tablet computer, having a gas sensor. The invention also relates to a method for operating such a device.

BACKGROUND ART

It has been known to incorporate gas sensors into portable sensor devices, such as mobile phones or tablet computers. For example, humidity sensors have been incorporated into some smartphone devices.

To reduce power consumption, devices of this type typically have a low-power and a high-power operating mode. In the low-power operating mode, the gas sensor is inoperative.

DISCLOSURE OF INVENTION

The problem to be solved by the present invention is to provide a device of the type mentioned above that exhibits better sensor performance.

This problem is solved by the subject matter of the independent claims.

Accordingly, the invention relates to a portable electronic device that has a CPU (i.e. a microcontroller or microprocessor) and a user interface (such as a graphical display) operated by the CPU. The device further comprises a gas sensor and, in addition to the CPU, a sensor hub. The sensor hub is adapted and structured to operate the gas sensor, e.g. by sending the gas sensor a command to execute a measurement and/or to read out the signal value generated by the gas sensor.

The device has a low-power and a high-power operating mode, wherein in said low-power operating mode the CPU has lower power consumption than in said high-power operating mode. In the low-power operating mode, the CPU is typically switched off or in a non-operating idle state. In the high-power mode, the CPU is operative.

Not only the device (and in particular the CPU) has a high- and a low-power operating mode, but also the gas sensor has a low-power and a high-power operating mode. In both operating modes, gas sensor is able to carry out measurements. However, it consumes typically more power and generates more accurate measurements in high-power operating mode than in low-power operating mode. The high- and low-power operating modes e.g. differ in the number of measurements taken by time unit, and/or in the duration of the heating pulses.

The sensor hub is adapted and structured to switch the device from low-power to high-power operating mode in response to a change of the signal from the gas sensor.

In other words, the sensor hub is able to wake the device up when the signal from the gas sensor changes in a certain manner.

Typically, the sensor hub comprises a microcontroller, i.e. a programmable processing unit adapted to sequentially process program code stored in a memory device.

Further, the sensor hub may comprise a memory location for storing a low-pass filtered value of a signal from the gas sensor and a comparator adapted to compare the low-pass filtered value to a current signal from said gas sensor. This allows to detect a sudden change in the signal from the gas sensor while allowing to ignore the slow signal drift that is typical for many types of gas sensors. The low-pass filtered value can e.g. be a moving average (rolling average) of the signal from the gas sensor.

The gas sensor can be integrated on the semiconductor substrate of a gas sensing device, together with processing circuitry. The microcontroller of the sensor hub is adapted to read the current signal from the processing circuitry. In such a design, the processing circuitry may take over part or all of the processing of the raw signal, thereby taking computative load from the microcontroller.

The method for operating the device according to the present invention comprises the step of switching the device from its low-power to its high-power operating mode in response to a change of signal from the gas sensor.

When the device is switched from its low-power to its high-power operating mode, the CPU can process the signal from the gas sensor. Since the CPU is typically more powerful than the sensor hub, such processing can provide more detailed information about the cause of the change in the signal.

It must be noted that the present invention can be viewed as method or a device. In particular, any of its features can be claimed as a method or a device, and it is apparent that any features formulated in the claims under one of these two categories can also be formulated in the claims under the other category.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

MODE FOR CARRYING OUT THE INVENTION

Figure 1:
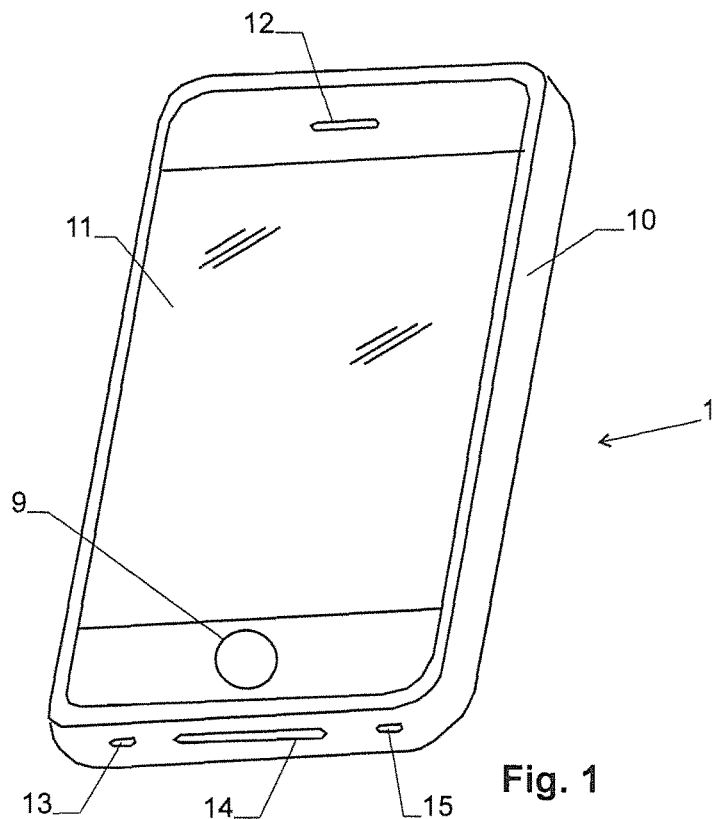
FIG. 1 is a perspective view of a portable electronic sensor device with a gas sensor.

Device Hardware:

The sensor device of FIG. 1 is a portable electronic device 1, such as a mobile phone. The housing 10 of the mobile phone includes a front side with a display 11 and input elements like buttons 9 to let a user interact with the phone. Also shown on the front side is an opening 12 for a loudspeaker. Further openings 13, 14 are located at a lower side wall of the housing 10. It is well known to mount components like microphones and loudspeakers behind such openings. A further opening 15, which is e.g. also arranged on the lower side wall of housing 10, provides access to a gas sensor as described in more detail below.

Figure 2:
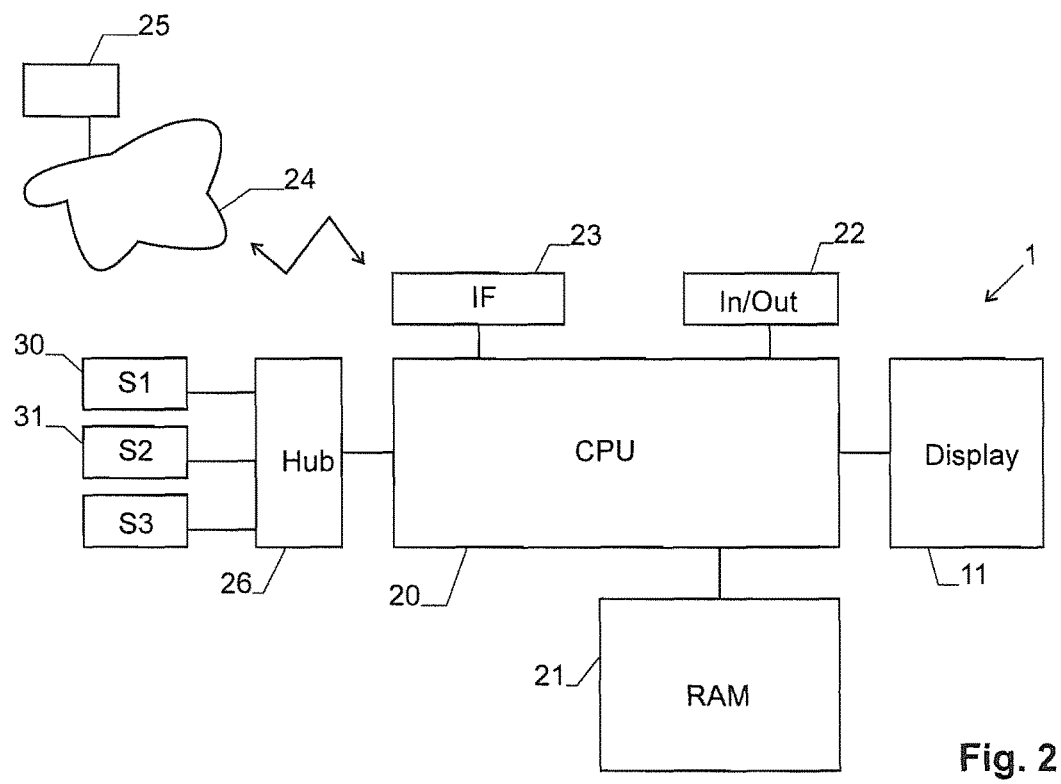
FIG. 2 is a block diagram of hardware components of the device.

FIG. 2 shows a block diagram with the most important components of the device. In particular, the device comprises a CPU 20 and non-volatile as well volatile memory 21 as known to the skilled person. FIG. 2 also shows the display 11 and a group 22 of further input- and output devices, such as the button 9, the loudspeaker and the microphones.

CPU 20 is adapted to execute software stored in memory 21 and to operate the user interface of the device, such as the display 11, e.g. by displaying information on display 11.

Further, the device comprises a network interface 23, which is capable to establish wireless data communication with an external network 24, such as the internet. This network is connected to further devices. At least one server device 25 of these further devices can be adapted to communicate with device 1 through network interface 23.

Device 1 further comprises a sensor hub 26 through which CPU 20 is able to communicate with a series of sensors S1, S2, S3 . . . . These sensors can e.g. comprise an accelerometer, one or more temperature sensors, and more. In particular, one of the sensors is a gas sensor 30. In an advantageous embodiment, a further sensor is a humidity sensor 31, such as described in U.S. Pat. No. 6,690,569.

Figure 3:
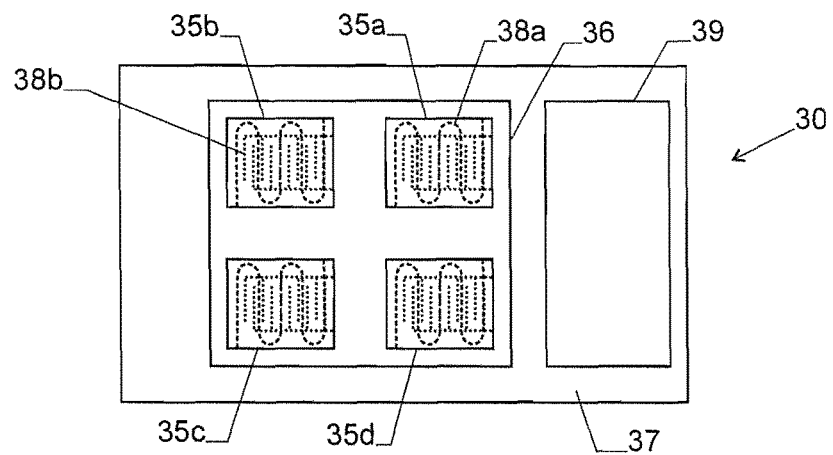
FIG. 3 shows a gas sensor in more detail.

Gas Sensor:

FIG. 3 shows an embodiment of a gas sensor 30. The shown sensor is e.g. a sensor basically of the type e.g. as described in WO 95/19563, where a sensing layer 35a, 35b, 35c, 35d, in particular of a metal-oxide, is arranged on a thin membrane 36 extending over an opening in semiconductor substrate 37.

In the embodiment of FIG. 3, there are four sensing layers 35a, 35b, 35c, 35d separately arranged on membrane 36, each of which forms a gas sensor of its own. The various sensing layers 35a, 35b, 35c, 35d can e.g. differ in their composition in order to measure different gas properties, thereby providing a richer data set for identifying individual analytes.

As mentioned, the sensing layers are advantageously metal-oxide (MOX) layers, such as layers of SnO. The MOX can also e.g. be tungsten oxide, gallium oxide, indium oxide, or zinc oxide, or a mixture of any of these materials, including SnO.

The sensing layers of the sensor of FIG. 3 require elevated temperatures for operation, typically of at least 100° C., for SnO-layers typically of at least 300° C. Hence, heaters 38a are provided for heating each of the sensing layers to its operating temperature.

As known to the skilled person, the conductance of the sensing layer 35a, 35b, 35c, 35d depends on the composition of the gas that surrounds it. Hence, interdigital electrodes 38b are provided for measuring the resistivity of the sensing layer 35a, 35b, 35c, 35d.

As shown in FIG. 3, gas sensor 30 further comprises processing circuitry 39 integrated on semiconductor substrate 37. This processing circuitry can e.g. comprise amplifiers and filters for processing the analog raw signal from the electrodes 38b, an A/D-converter for converting the processed analog signal, and digital circuitry for processing the digitized signal. The digital circuitry may e.g. comprise a linearizer for linearizing the raw signal, as well as an interface for accessing the processed signal and for receiving operating commands and operating parameters.

Figure 4:
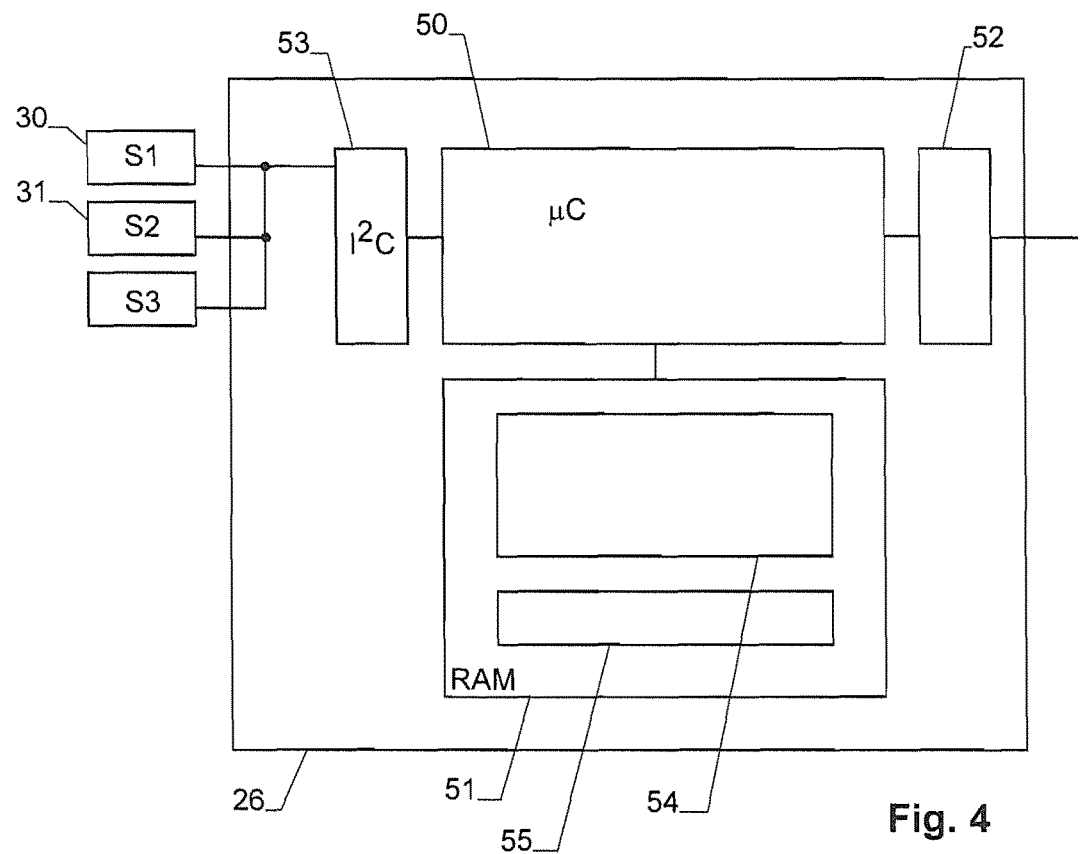
FIG. 4 is a block diagram of an embodiment of a sensor hub.

Sensor Hub:

FIG. 4 is a block circuit diagram of sensor hub 26. In the present embodiment, sensor hub 26 is formed by a single microcontroller having a programmable microcontroller core 50, memory 51, a first interface 52 for connecting it to CPU 20, and a second interface 53, such as a I²C-interface, for connecting it to the sensors 30, 31, etc.

Core 50 is adapted to run program code 54 stored in memory 51.

Instead of being formed by a single microcontroller, sensor hub 26 may also be formed by discrete components, such as a microcontroller with external memory and interface circuitry.

The microcontroller of sensor hub 26 is adapted to run separately from CPU 20, i.e. it can operate even when CPU 20 is switched off. Typically, it has much lower processing power than CPU 20, but it is optimized for low-power operation and can be run much more frequently or even continuously without giving rise to an excessive power drain.

Figure 5:
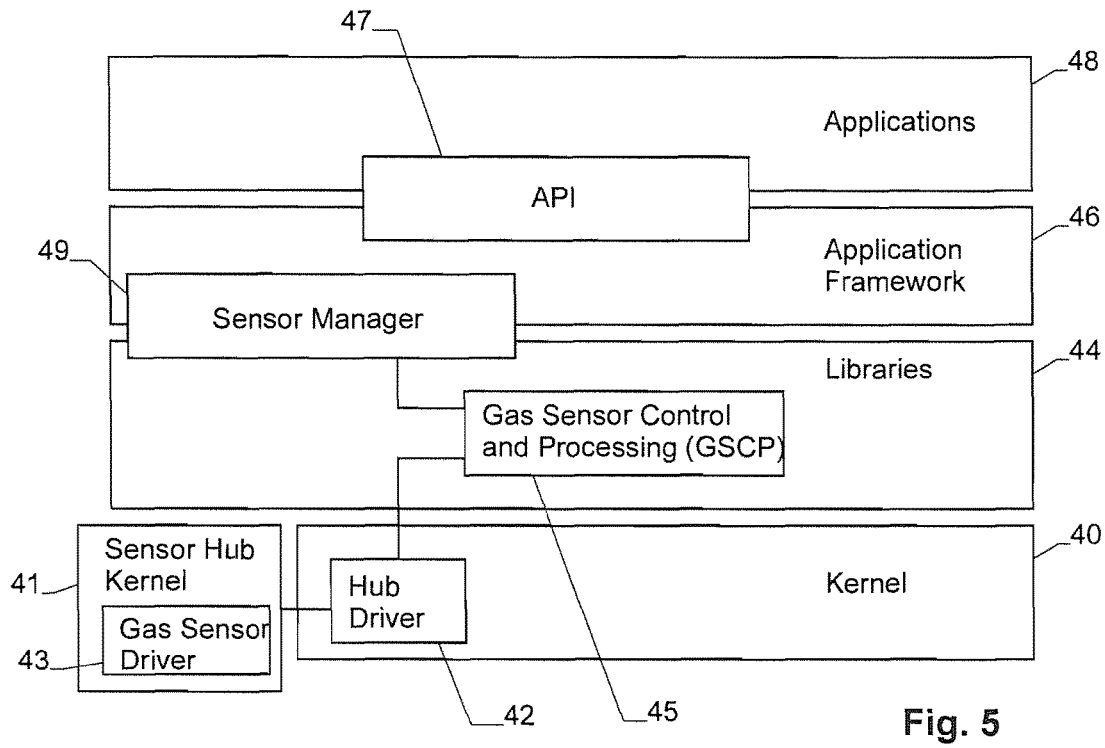
FIG. 5 is a block diagram of software components of the device, and FIG. 6 a flow chart of the steps executed by the sensor hub in low-power mode.

Device Software:

FIG. 5 shows the—for the present context—most relevant components of the software stack of the device. As can be seen, the software stack comprises a kernel 40 adapted to provide low-level functionality. The kernel e.g. comprises the individual device drivers adapted to interact with individual hardware components of the device.

The microcontroller of sensor hub 26 runs its own kernel software 41, which is typically loaded into memory 51. The sensor hub kernel software interacts with a hub driver 42 of the main kernel 40. The driver 43 for driving the gas sensor 30 is implemented in the hub kernel software 41. It must be noted, though, that driver 43 could also be implemented, at least in part, in the main kernel 40.

A library level 44 sits on top of kernel 40. It comprises a number of libraries, with each library providing functionality that is, at least to a certain degree, typically machine independent (in contrast to the kernel software which is typically adapted to the hardware of the device where it is running). As known to the skilled person, the operating system's runtime is typically implemented in at least one of these libraries.

Each library comprises typically one or more code files comprising code that can be dynamically or statically linked to other libraries or to applications. Typically, libraries are implemented as dynamically linked libraries (DLLs).

One library in library level 44 is the gas sensor control and processing library (GSCP) 45. Its purpose is to control the operation of gas sensor 30 and to process its signals.

On top of library level 44 sits the application framework 46, which is typically also implemented as a set of libraries. In contrast to most of the libraries in library level 44, the libraries of the application framework 46 provide a public interface 47 (the Application Programming Interface, API) available to the topmost software level, the applications 48.

Part of the application framework is a sensor manager 49, which defines the part of the API that relates to the sensors of device 1 and which interacts with the sensor-related libraries and drivers in libraries level 44 or in kernel 40.

The applications 48 are typically provided by third parties (i.e. neither by the hardware manufacturer nor by the provider of the operating system). They link against the libraries laid open in the API on order to execute specific tasks.

For example, one such application may be an application that is supposed to detect a certain gas or to analyse the composition of the gases in contact with gas sensor 30. Such an application would use the sensor manager's 49 API in order to interact with gas sensor 30.

Power Management:

Device 1 has a low-power and a high-power mode. In low-power mode, CPU 20 is switched off or is in an idling mode where its power consumption is zero or at least reduced as compared to the normal high-power operating mode. In this mode, CPU 20 is typically unable to process any data, or, at best, it processes data at a much slower rate than in normal operation. In high-power mode, CPU 20 is running normally, processes data and runs programs, typically continuously, and operates display 11, e.g. in accordance to command issued by the application programs that are currently operative.

Sensor hub 26 is running in low-power as well as high-power mode of device 1. The steps executed by the microcontroller of sensor hub 26 in low-power and high-power mode may differ, or they may be the same.

Figure 6:
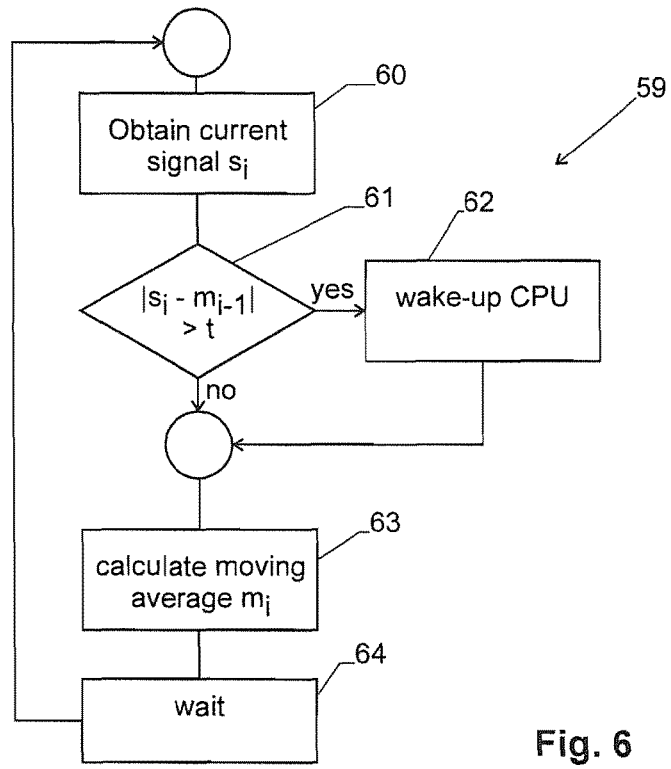

FIG. 6 shows the steps executed by the microcontroller in relation to the gas sensor, at least in low-power mode.

As can be seen, the microcontroller operates a loop 59 repetitively. In the following, it is assumed that index i designates the index of the current iteration of loop 59.

In a first step 60 when executing the loop, the microcontroller obtains the current signal value $s_i$ from gas sensor 30. This current signal value can e.g. be directly derived from the conductance measured for one of the sensor layers 35a, 35b, 35c, 35d, or an average of the conductance of these layers.

In step 61, the change of the measured signal is calculated by computing the absolute value of the difference between the currently measured value $s_i$ and the previous moving average $m_{i-1}$ of this value (definition see below) and by comparing this difference to a threshold t, i.e. the following Boolean expression is evaluated:

$$|s_i - m_{i-1}| > t \quad (1)$$

Such a comparison is carried out by a comparator, such as implemented by the hardware of core 50.

If it is found in step 61 that the change exceeds threshold t, step 62 is executed to wake up CPU 20 if the device is in its low-power mode.

In a next step 63, a new value for the moving average $m_i$ is calculated, e.g. from $$m_i = m_{i-1}*(N-1)/N + s_i/N \quad (2)$$

with $m_i$ being the moving average calculated in iteration $m_{i-1}$ is the moving average of the previous iteration and N is an integer that is much larger than 1, e.g. at least 10. Eq. (2) describes the cumulative moving average. Other methods for calculating a moving average or for low-pass filtering the measured signals in other manner, such as the simple moving average or a weighted moving average, can be used as well. A typical averaging time should be larger than the response time of the gas sensor, but it should be much smaller than the time during which a gradual drift of the gas sensor occurs. Typically, the averaging time, i.e. the time span that contributes to at least 90% of the moving average, should be at least 1 minute but it should be smaller than 12 hours, in particular between 1 and 10 hours. This takes into account that the concentration of noxious gases typically takes some time to build up in a room, and a good averaging can e.g. be carried out when the device is in rest e.g. during one night.

The moving average $m_i$ is stored in a suitable memory location 55 of memory 51 or of core 50.

Loop 59 ends in step 64, where it is interrupted for a certain time interval, e.g. for one or a few seconds, in order to decrease the power consumption of sensor hub 36.

Notes:

In the above embodiment, the change of the sensor signal, e.g. expressed by Eqs. (1) and (2), is calculated by the microcontroller of sensor hub 36. Alternatively, such a moving average can e.g. be calculated by processing circuitry 39 of sensing device 30, in which case sensor hub 36 can have a simpler design.

Once that CPU 20 is woken up after a change of the sensor signal of gas sensor 30, it retrieves the current sensor signal through sensor hub 36 and processes it more thoroughly, optionally by executing further measurements, in order to gain a better understanding of the reason why the signal has changed.

Advantageously, not only device 1 (and in particular CPU 20) has a high- and a low-power operating mode, but also gas sensor 30 has a low-power and a high-power operating mode. In both operating modes, gas sensor 30 is able to carry out measurements. However, it consumes more power and generates more accurate measurements in high-power operating mode than in low-power operating mode. The high- and low-power operating modes e.g. differ in the number of measurements taken by time unit, and/or in the duration of the heating pulses. While device 1 is in low-power mode, gas sensor 30 is also in low power operating mode. Once that CPU 20 is woken up, it sets gas sensor 30 into high-power operating mode, at least during an initial analysis stage, to obtain more accurate results.

Depending on the result of this processing, CPU 20 may e.g. issue an alert, in particular an audible or visible alert and/or a message through network interface 23. This is especially useful if it was found that the change is due to a rise of the concentration of some noxious substance, such as CO or flue gas.

In summary, in one embodiment, the mobile device comprises a CPU 20 operating a display 11 and other user interface circuitry. Further, it comprises a gas sensor 30 as well as a sensor hub 26 connecting the gas sensor 30 and other sensors to CPU 20. In order to save power, the device can be brought into a low-power operating mode, where CPU 20 is idling or switched-off. However, even in this low-power operating mode, sensor hub 26 still monitors for changes of the signal from gas sensor 30 and wakes the device up if such a change is detected.

While there are shown and described presently preferred embodiments of the invention, it is to be distinctly understood that the invention is not limited thereto but may be otherwise variously embodied and practised within the scope of the following claims.

The invention claimed is:

1. A portable electronic device, in particular a mobile phone or tablet computer, wherein said portable sensor device comprises a CPU, a user interface operated by said CPU, a gas sensor for taking measurements of gas surrounding the sensor and generating signals therefrom, and a sensor hub, in addition to said CPU, said sensor hub being adapted and structured to operate said gas sensor, wherein said device has a low-power and a high-power operating mode, wherein in said low-power operating mode said CPU has lower power consumption, lower processing power and lower processing rate than in said high-power operating mode, wherein said sensor hub operates separately from said CPU in both said low-power and high-power operating modes, has lower processing power than said CPU, and is adapted and structured to switch said device from said low-power to said high-power operating mode in response to a change of signal from said gas sensor, wherein said gas sensor has a low-power and a high-power operating mode, wherein said gas sensor consumes more power and generates more accurate measurements in said high-power operating mode than in said low-power operating mode, and wherein said gas sensor is in said low-power operating mode while said device is in said low-power operating mode, but said gas sensor is set into said high-power operating mode after switching said device from said low-power to said high-power operating mode, and wherein, once said device is switched from said low-power mode to said high-power operating mode as aforesaid, said CPU retrieves a current sensor signal through said sensor hub and processes it by executing further measurements.

2. The device of claim 1 wherein said sensor hub comprises a microcontroller core.

3. The device of claim 2 comprising a gas sensing device having a semiconductor substrate, wherein said gas sensor is integrated on said semiconductor substrate, wherein said gas sensing device further comprises processing circuitry integrated on said semiconductor substrate, wherein said microcontroller is adapted to read said current signal from said processing circuitry.

4. The device of claim 1 wherein said sensor hub comprises a memory location for storing a low-pass filtered value of a signal ($m_{i-1}$) from said gas sensor and a comparator adapted to compare said low-pass filtered value ($m_{i-1}$) to a current signal ($s_i$) from said gas sensor.

5. The device of claim 4 wherein said sensor hub is adapted to switch said device from said low-power to said high-power operating mode if a difference between said filtered value ($m_{i-1}$) and said current signal ($s_i$) exceeds a given threshold value (t).

6. The device of claim 4 wherein said sensor hub is adapted to calculate a moving average ($m_i$) value of the signal from said gas sensor.

7. The device of claim 6 wherein said moving average spans a time between 1 minute and 12 hours, in particular between 1 hour and 10 hours.

8. The device of claim 1 wherein, in said low-power mode, said CPU is switched off.

9. The device of claim 1 wherein said gas sensor has a heater providing heating pulses, and wherein the low-power operating mode and a high-power operating mode of said gas sensor differ in the number of measurements taken per time unit, and/or in the duration of the heating pulses.

10. The device of claim 1 wherein said gas sensor comprises a metal-oxide sensing layer.

11. A method for operating the device of claim 1 comprising the step of switching said device from said low-power to said high-power operating mode in response to a change of signal from said gas sensor, wherein said CPU processes the signal from the gas sensor as aforesaid after said device is switched from said low-power to said high-power operating mode.

12. The method of claim 11 further comprising the step of issuing an alert, in particular an audible or visible alert, by said device, if the cause of the change is due to a rise of a concentration of a noxious substance.

* * * * *